United States Patent [19]

Gomez et al.

[11] Patent Number: 5,070,880
[45] Date of Patent: Dec. 10, 1991

[54] TRANSCRANIAL DOPPLER TRANSDUCER HOUSING STABILIZER

[75] Inventors: Camilo R. Gomez, Manchester, Mo.; James R. McLaughlin, Franklin, Pa.

[73] Assignee: St. Louis University, St. Louis, Mo.

[21] Appl. No.: 606,066

[22] Filed: Oct. 30, 1990

[51] Int. Cl.⁵ .............................................. A61B 8/00
[52] U.S. Cl. ........................... 128/661.08; 128/662.03; 128/660.09
[58] Field of Search ...................... 128/661.08, 662.03, 128/660.09, 660.01; 73/861.25, 861.28, 861.26

[56] References Cited

U.S. PATENT DOCUMENTS

| | | | |
|---|---|---|---|
| 4,483,344 | 11/1984 | Atkov et al. | 128/662.03 |
| 4,817,621 | 4/1989 | Aaslid | 128/662.03 |
| 4,920,966 | 5/1990 | Hon et al. | 128/662.03 |
| 4,947,853 | 8/1990 | Hon | 128/662.03 |

Primary Examiner—Francis Jaworski
Assistant Examiner—George Manuel
Attorney, Agent, or Firm—Senniger, Powers, Leavitt & Roedel

[57] ABSTRACT

A transducer housing stabilization device for supporting a transcranial Doppler transducer against a temporal bone of a head. The device includes a generally planar, rigid member having an opening therein. The member has perforations therein for engaging an adhesive to secure the planar member adjacent to the temporal bone of the head. A transducer housing on the member receives the transducer thereby positioning the transducer in place adjacent the temporal bone of the head.

20 Claims, 2 Drawing Sheets

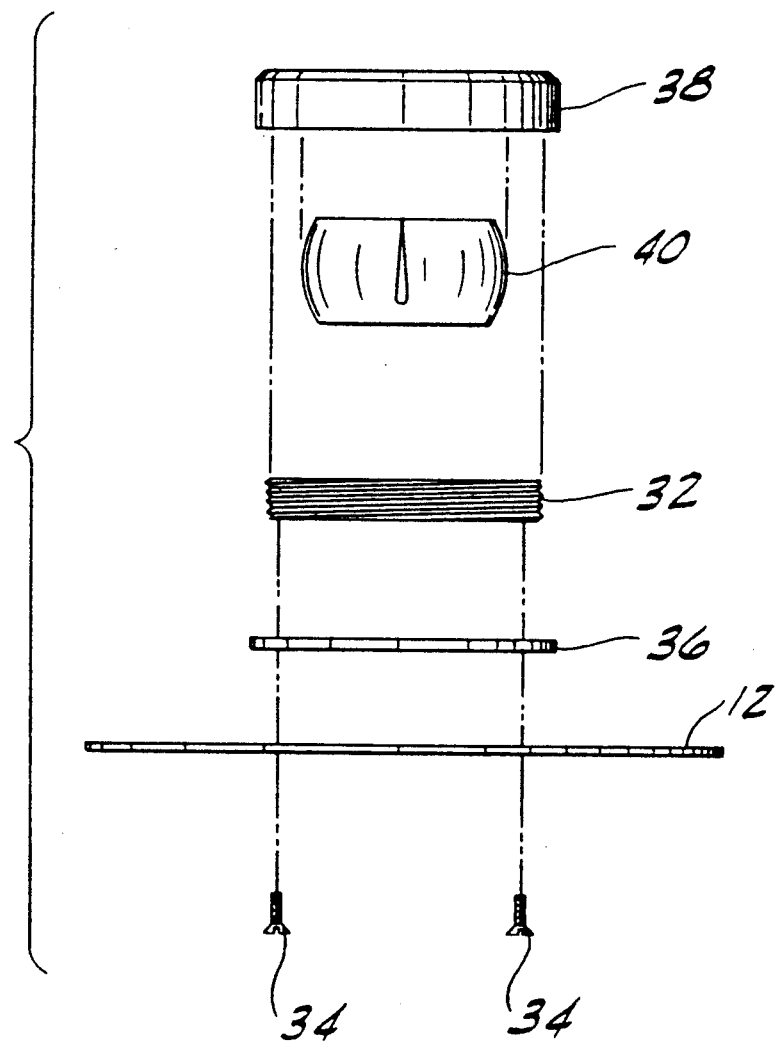

TRANSCRANIAL DOPPLER TRANSDUCER HOUSING STABILIZER

FIELD OF THE INVENTION

This invention relates generally to ultrasonography of cerebrovascular physiology and more particularly to a probe stabilizer for measuring transcranial Doppler signals.

BACKGROUND OF THE INVENTION

Transcranial Doppler (TCD) ultrasonography has gained widespread acceptance as a non-invasive method for the evaluation of cerebrovascular physiology such as monitoring of blood flow velocities from any of the vessels accessible through the transtemporal window. A major disadvantage of TCD ultrasonography is that the patients must be cooperative and somewhat still during insonation, in order to assure adequate sampling of Doppler signals. Attempts to carry out such monitoring have met with the obstacle of proper stabilization of the TCD transducer. Even under conditions of relative patient immobility, i.e., during surgical procedures, various investigators have reported difficulties obtaining accurate blood flow velocity measurements. The major problem noted has been probe displacement during continuous monitoring. In an attempt to overcome this, several somewhat cumbersome methods for stabilizing TCD transducer housings have been developed with variable success and their own inherent limitations. There is a need for a simple yet reliable TCD transducer housing stabilizer which is practical and which allows continuous monitoring without regard to patient position or head movement.

SUMMARY OF THE INVENTION

Among the several objects of the invention may be noted a simple yet reliable TCD transducer housing stabilizer which allows continuous TCD monitoring of blood flow velocities from any of the vessels accessible through the transtemporal window without regard to patient position or head movement.

It is a further object of this invention to provide a simple yet reliable TCD transducer housing stabilizer which can be disconnected and reconnected to an ultrasound transducer without changing the quality of the ultrasound waveforms generated by the transducer.

It is a further object of this invention to provide a TCD transducer housing stabilizer which permits continuous transtemporal TCD monitoring in a variety of experimental and clinical situations.

It is another object of this invention to provide a TCD transducer housing stabilizer which is simply constructed, easily applied to the patient and which permits continuous transtemporal TCD monitoring in the supine, prone, lateral decubitus or head-down positions, at rest or during activity with virtually no restrictions on head movement.

It is yet another object of this invention to provide such a stabilizer which permits measurements during flexion, lateral rotation and tilting of the neck while providing preservation of the Doppler waveforms during all these maneuvers.

The invention comprises a stabilization device for supporting a transcranial Doppler transducer housing adjacent to a temporal bone of a head. A generally planar member has an opening therein. Means on the member engages an adhesive on a portion of the head adjacent to the temporal bone of the head to secure the member adjacent to the temporal bone of the head. A transducer housing on the member receives the transducer and supports the transducer within the opening and in place adjacent the temporal bone of the head when the member is secured to the temporal bone of the head.

BRIEF DESCRIPTION OF THE DRAWINGS

Other objects of the present invention and their attendant advantages will become readily apparent from the following description taken in conjunction with the accompanying figures in which like reference characters are used to describe like parts throughout the several views:

FIG. 4 is an exploded, side view of the elements of the device of the invention.

DETAILED DESCRIPTION OF A PREFERRED EMBODIMENT

Figure 1:
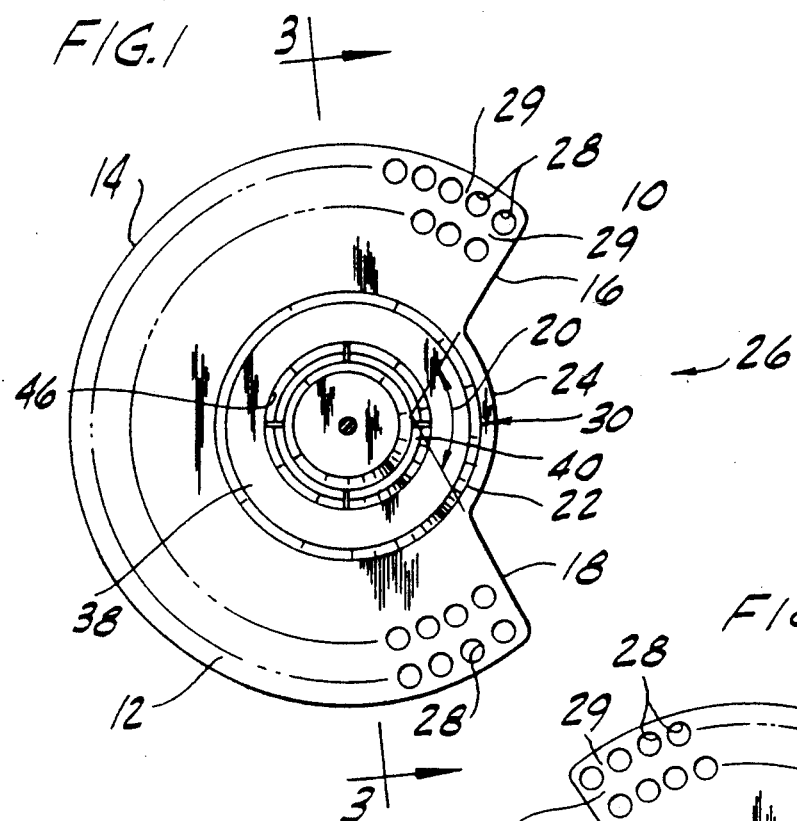
FIG. 1 is a top plan view of the portion of the device of the invention which, when mounted to the head, faces away from the temporal bone of the skull.
Figure 2:
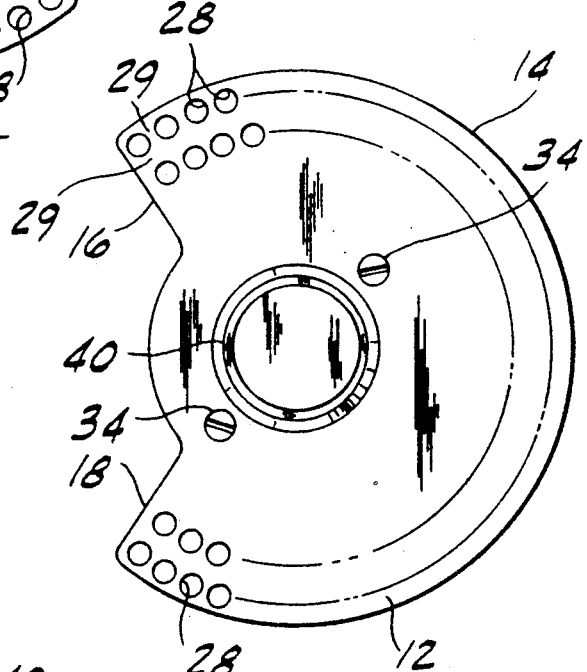
FIG. 2 is a bottom Plan view of the portion of the device of the invention which, when mounted to the head, is placed against the temporal bone of the skull.

Referring now to the drawings, and more particularly to FIGS. 1 and 2, a stabilization device 10 according to the invention is illustrated. It includes a partially circular, substantially rigid, stainless steel plate 12. The majority of the perimeter 14 of the plate 12 defines an edge forming a large circular arc of about 270°. Straight edges 16 and 18 extend from each of the two ends of the perimeter 14 toward the inside of the arc. The straight edges 16 and 18 form an obtuse angle 20 when extended to intersect with each other. The plate 12 has a centrally located, substantially round opening 22 therein. Preferably, the straight edges 16 and 18 are, when extended, tangent to the opening 22 and are joined by an arcuate edge 24 to form a notch 26 in the plate 12. The notch 26 is for receiving an ear adjacent the temporal bone of the skull when the planar member is secured to the temporal bone of the head.

In addition, the plate includes a plurality of perforations 28 in the form of an array of equally spaced openings distributed throughout the plate 12. The perforations 28 are interconnected by bridge elements 29 which, with the perforations, constitute means on the plate 12 for engaging an adhesive on a portion of the head adjacent to the temporal bone of the head to secure the plate 12 to the temporal bone of the head.

Figure 3:
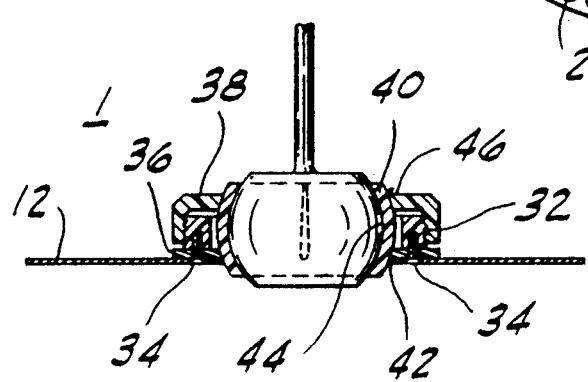
FIG. 3 is a cross-sectional view of the invention taken on the line 4—4 of FIG. 1 and FIG. 2.

The stabilization device 10 includes a housing 30, axially positioned about the central opening 22, illustrated in detail in FIGS. 3 and 4. Externally threaded tubular element 32 is mounted to plate 12 by screws 34 and is spaced from plate 12 by base washer 36. Internally threaded nut 38 engages the threads of element 32. Positioned between nut 38 and base washer 36 is a compression collar 40 which is radially inwardly compressed as the nut 38 is tightened onto the tubular element 32. In particular, tightening of nut 38 onto tubular element 32 causes edges forming an internal opening 42 of base washer 36 to act as a cam against the curved outer surface 44 of the compression collar 40. It also causes an internal edge defining an opening 46 in nut 38 to radially inwardly compress the compression collar 40. As a result, base washer 36 and nut 38 function as lockdown washers to hold collar 40 in place with respect to plate 12. Collar 40 includes a slot 48 therein which closes as the collar is compressed. Positioned within the collar 40 is a transcranial Doppler transducer 50 which is held in place by the compression of the collar 40. The transducer 50 may preferably extend below a plane defined by plate 12 so that transducer 50 is in contact with the temporal bone of a skull when the device 10 is mounted to a skull. As is apparent from the drawings, central opening 22 of plate 12, internal opening 42 of base washer 36, and opening 46 of nut 38 are coaxially aligned for receiving collar 40.

Use of the TCD transducer stabilization device 10 requires prior identification of the location of the transtemporal window on the head such as by using a handheld transducer. The position of the window on the skin is then marked. In principle, the most important points of adhesion to ensure maximum stability of the device 10 are over the zygoma, squamous portion of the temporal bone at the superior root of the pinna, and circumferentially about the base of the transducer housing. While shielding the ipsilateral eye, the device is affixed to the skin surface by filling the perforations 28 in the plate 12 with collodion and applying it to the shin so that the straight edges 14, 16 of the wedge-shaped notch 26 juxtapose the superior root of the pinna. The collodian is quickly dried using a forced air compressor. The process of fixation of the device requires approximately five (5) minutes. A flat TCD monitoring transducer is then inserted into the collar 40 of housing 30, an optimal signal is obtained and the lockdown nut 38 is tightened, thus securing the transducer alignment with respect to the plate 12. The subject is then ready for continuous monitoring. Upon cessation of monitoring the device 10 is removed within approximately five (5) minutes by rubbing acetone or other solvent on the surface of plate 12 with a cloth and exerting a minimal amount of traction on the plate 12. This results in applying solvent to the adhesive in the perforations, dissolving the adhesive and permitting the device 10 to be detached from the skin.

The process of its application and removal is rapid and efficient because its fundamental principle is "glueing" the device 10 to the head using collodion. The latter has been safely used for years as the most reliable method of securing electroencephalographic electrodes in place, even during long-term monitoring.

This method of fixation eliminates the inherent inaccuracies related to failure of insonation at the same site with serial recordings, the time delay between physiologic change and TCD measurement and the probe displacement occurring during continuous monitoring. It allows the dynamic investigation of cerebrovascular physiology and pathophysiology, and it affords the opportunity to observe the effect of pharmacological and physiological manipulation of the cerebral circulation under experimental, surgical and critical care conditions.

We claim:

1. A stabilization device for supporting a transcranial Doppler transducer adjacent a temporal bone of a head, said device comprising:

a generally planar, substantially rigid member having an opening therein and having perforations therein defining means for engaging an adhesive to secure the member adjacent to the temporal bone of the head; and a transducer housing on the member for receiving the transducer and for supporting the transducer within the opening and in place adjacent the temporal bone of the head when the member is secured to the temporal bone of the head by the adhesive.

2. The device as set forth in claim 1 further comprising an adhesive attaching the engaging means to the head and wherein said transducer housing comprises a compressible collar for receiving the transducer and means for radially inwardly compressing the collar to engage the transducer.

3. The device as set forth in claim 2 wherein the compressing means further comprises a washer coaxial with the opening, an externally threaded tubular element on the member and coaxial with the washer and opening, and an internally threaded nut engaging the threads of the tubular element and having an opening coaxial with the tubular element, the openings of the washer and nut forming rims engaging an exterior surface of the collar and causing radially inward compression of the collar as the nut is tightened on the tubular element.

4. The device as set forth in claim 3 comprising a plurality of fasteners for mounting the tubular element to the planar member.

5. The device as set forth in claim 3 wherein the planar member comprises a substantially rigid stainless steel plate.

6. The device as set forth in claim 3 wherein the planar member has a notch therein for receiving an ear when the planar member is secured to the temporal bone of the head.

7. The device as set forth in claim 6 wherein the notch is defined by inwardly directed straight edges joined by a arcuate edge.

8. The device as set forth in claim 7 wherein the straight edges form an obtuse angle and are substantially tangent to the opening in the planar member.

9. The device as set forth in claim 1 wherein the planar member has a notch therein for receiving an ear when the planar member is secured to the temporal bone of the head.

10. The device as set forth in claim 9 wherein the notch is defined by inwardly directed straight edges joined by a arcuate edge.

11. The device as set forth in claim 10 wherein the straight edges form an obtuse angle and are substantially tangent to the opening in the planar member.

12. A method of using a transcranial Doppler transducer on a temporal bone of the head comprising the steps of:

providing a transducer housing having a perforated portion;

locating the transtemporal window;

applying adhesive to the perforated portion and to the skin adjacent the transtemporal window;

affixing the perforated portion on the head adjacent the temporal bone so that the adhesive is located in at least some of the perforations therein; and positioning the transducer within the housing so that the transducer is adjacent the temporal bone of the head.

13. The method as set forth in claim 12 including the step of removing the housing by the steps of:

applying solvent to the adhesive in the perforations;

dissolving adhesive within the perforations; and detaching the perforated portion from the skin.

14. The method as set forth in claim 12 wherein the housing includes a compressible collar for engaging the transducer and wherein the positioning step includes locating the transducer within the collar and compressing the collar to firmly affix the transducer within the housing.

15. A stabilization device for supporting a transcranial Doppler transducer housing adjacent a temporal bone of a head, said device comprising:
   a generally rigid member having an opening therein and having a notch therein defining means for receiving an ear when the rigid member is secured to the temporal bone of the head; and
   a transducer housing on the member for receiving the transducer and for supporting the transducer within the opening and in place adjacent the temporal bone of the head when the member is secured to the temporal bone of the head.

16. The device as set forth in claim 15 further comprising means for engaging the member and a portion of the head adjacent to the temporal bone of the head to secure the member adjacent to the temporal bone of the head.

17. The device as set forth in claim 16 wherein the engaging means comprises collodian.

18. A stabilization device for supporting a transcranial Doppler transducer adjacent a temporal bone of a head, said device comprising:
   a generally rigid planar member having an opening therein;
   an adhesive on a portion of the head adjacent to the temporal bone of the head;
   means on the member for engaging the adhesive to secure the member adjacent to the temporal bone of the head; and
   a transducer housing on the member for receiving the transducer and for supporting the transducer within the opening and in place adjacent the temporal bone of the head when the member is secured to the temporal bone of the head.

19. A stabilizer for a transcranial Doppler transducer housing for supporting a transcranial Doppler transducer adjacent a temporal bone of the head, said stabilizer comprising:
   an adhesive on the head;
   a generally rigid planar member having an opening therein and having perforations therein engaging the adhesive to secure the member adjacent to the temporal bone of the head; and
   means for engaging the transducer housing so that the housing supports the tranducer within the opening and in place adjacent the temporal bone of the head when the member is secured to the temporal bone of the head by the adhesive.

20. A stabilizer for a transcranial Doppler transducer housing for supporting a transcranial Doppler transducer adjacent a temporal bone of the head, said stabilizer comprising:
   a generally rigid member having an opening therein and having a notch therein defining means for receiving an ear when the rigid member is secured to the temporal bone of the head; and
   means for engaging the transducer housing so that the housing supports the transducer within the opening and in place adjacent the temporal bone of the head when the member is secured to the temporal bone of the head by the adhesive.

* * * * *